United States Patent [19]

Ley et al.

[11] Patent Number: 4,923,804

[45] Date of Patent: May 8, 1990

[54] *ESCHERICHIA COLI (E. COLI)* TEST METHOD

[75] Inventors: Arthur N. Ley; Neil E. Rickey; Michael J. Taylor, all of Kingston, Canada

[73] Assignee: Queen's University at Kingston, Kingston, Canada

[21] Appl. No.: 39,435

[22] Filed: Apr. 17, 1987

[30] Foreign Application Priority Data

Mar. 17, 1987 [CA] Canada .................................... 532191

[51] Int. Cl.$^5$ .............................................. C12Q 1/10
[52] U.S. Cl. ........................................ 435/38; 435/29; 435/30; 435/34; 435/18; 435/849
[58] Field of Search ................... 435/18, 29, 34, 849, 435/38, 810, 803; 536/17.3, 17.4, 18.1

[56] References Cited

U.S. PATENT DOCUMENTS 4,277,561 7/1981 Monget et al. ........................ 435/24

FOREIGN PATENT DOCUMENTS 0025467 3/1981 European Pat. Off. .
0122028 3/1984 European Pat. Off. .

OTHER PUBLICATIONS

Anderson et al., Substrates for the Histochemical Localization of Some Glycosidases, 1961, pp. 236-238.
Pearson et al., "*Histochemical β-Glucuronidase Distribution in Mammalian Tissue as Detected by 5-Bromo-4-Chloroindol-3-yl-β-D-Glucopyruroniside*", 1967, vol. 17, No. 2, pp. 217-224 of the periodical entitled Laboratory Investigation.

*Primary Examiner*—Sam Rosen
*Attorney, Agent, or Firm*—Richard J. Hicks

[57] ABSTRACT

The present invention provides a method which is specific to determining and is capable of enumerating *Escherichia coli* (*E. coli*) in a sample water or sewage specimen. The method comprises adding to a cultured specimen a chromogenic reagent which when subjected to in situ *E. coli* β-glucuronidase activity produces clearly defined vivid colorization of any individual colonies derived from *E. coli* cells in the test specimen.

5 Claims, No Drawings

ESCHERICHIA COLI (E.COLI) TEST METHOD

CROSS REFERENCE TO RELATED APPLICATION

This application is related to copending application Ser. No. 080,731 filed 3 Aug. 1987 now abandoned.

FIELD OF THE INVENTION

The present invention relates to a method of determining both qualitatively and quantitatively the presence of *Escherichia coli* (*E. coli*) in a test specimen.

BACKGROUND OF THE INVENTION

Communicable disease-causing organisms can be present at very high cell densities in the feces of infected humans and animals and water that is contaminated with sewage or fecal wastes poses a serious threat to human health.

There are presently available different methods for testing the sanitary quality of water. These methods include monitoring for indicator bacteria which are naturally present at high levels in the feces of humans and animals but which are not found in unpolluted or potable water supplies.

A primary drawback of most existing tests to determine the presence of sewage is that they are not specific to locating indicator bacteria of fecal origin, but rather also indicate other strains which do not necessarily originate in the intestines of warm-blooded animals, nor do they always come from man. Two commonly used bacterial indicator tests for determining the sanitary quality of water are the total coliform and fecal coliform procedures. These tests, however, give positive reactions for a group of bacteria which may not have been derived from feces. Included in the total coliform group are certain strains which are generally not found in fecal material, such as Klebsiella, Enterobacter, Citrobacter genera which may be found in soils and on vegetation and which are infrequently isolated in feces and then only in a very small amount. The fecal coliform group, which is comprised principally of the bacterium *Escherichia coli*, and which is the predominant fecal coliform found in feces, does include to a very lesser extent Klebsiella and Enterobacter so that a test result showing the presence of fecal coliforms may or may not indicate fecal contamination and follow-up investigation is the only accurate method of verifying the test results.

There are presently available test procedures which do verify the presence of fecal discharge in a test sample based on the specific determination of *E. coli*. *E. coli* is a common and natural inhabitant of the intestines of humans and animals and is present at a cell density in the range of $10^7$ to $10^8$ cells per gram of feces. These test methods include the use of fluorogenic and chromogenic chemicals namely, 7-hydroxy-4-methylcoumarin-7-β-D-glucuronide and p-nitrophenyl-β-D-glucuronide. These chemicals, although highly selective of *E. coli*, do not produce results for easily enumerating or quantifying the amount of *E. coli* present in a test specimen. In particular, the former chemical, otherwise known as MUG, fluoresces, thus requiring the use of a fluorescent light for analysis. This fluorescent light can be subject to interference in a membrane filter test and may result in poor accuracy of enumeration. The latter chemical, also known as PNG, is again not suitable for the enumeration of distinct *E. coli* colonies as the colour which develops during bacterial growth is not retained within the colony, but rather spreads throughout the entire test specimen making it impossible to count individual colonies.

SUMMARY OF THE PRESENT INVENTION

The present invention provides a method of determining the presence of and which is capable of enumerating *E. coli* in a test specimen comprising interacting the specimen and a chromogenic reagent which when subjected to *E. coli* β-glucuronidase (β-D-glucuronide glucuronohydrolase, EC 3.2.1.31 or β-D-glucuronoside glucuronosohydrolase) activity produces clearly defined colouring representative of any individual colonies derived from *E. coli* cells present in the test specimen.

The chromogenic reagent of the present invention is selected from the group of reagents having the formula:

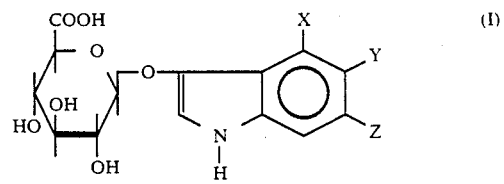

where X, Y and Z are the same or different and are selected from the group consisting of hydrogen, halogen, trihalogenated alkene, trihalomethyl, nitro, saturated or unsaturated alkyl, and aryl; and salts thereof including the alkali metal, lower alkyl ammonium, and lower aryl ammonium salts thereof.

DETAILED DESCRIPTION ACCORDING TO THE PREFERRED EMBODIMENTS OF THE PRESENT INVENTION

According to an aspect of the present invention, the method is carried out using a standard membrane filtration analysis as has been described in the Ontario Ministry of the Environment-Hand Book of Analytical Methods of Environmental Samples, December 1983. In this membrane filtration method, the chromogenic reagent, if subjected to β-glucuronidase activity as a result of the presence of *E. coli*, produces clearly defined colouring on the membrane filter representative of individual colonies grown from *E. coli* cells in the test specimen. These coloured colonies are readily countable to indicate the degree of *E. coli* contamination of the test specimen.

According to a preferred embodiment of the present invention the chromogenic reagent comprises indoxyl-β-D-glucuronide or a salt thereof which when interacted with β-glucuronidase produces a sharp clearly outlined indigo blue colouring of the individual *E. coli* colonies.

The present invention is highly selective of *E. coli*, because the chromogenic reagent only responds to β-glucuronidase activity which does not occur in fecal coliform bacteria other than *E. coli*. In the group of *E. coli* strains, the overwhelming majority are glucuronidase-producing, with only rare exceptions.

In a preferred embodiment of the present invention indoxyl-β-D-glucuronide or its chemically equivalent salts or other analogues is interacted with a specimen cultured in an appropriate nutrient medium with a ratio of about 0.3 to 0.8 grams chromogenic reagent per liter of nutrient medium to be tested for *E. coli*. If *E. coli* is present the β-glucuronidase enzyme produced thereby cleaves the indoxyl moiety from the glucuronide moiety thereby producing the aglycone 3-hydroyxindole or its chemical equivalent. This oxidizes to form the blue dye indigo which, when the test is conducted on a membrane filter, shows up in readily countable individual colonies grown from the *E. coli* cells.

The most preferred chromogenic reagent namely, indoxyl-β-D-glucuronide or its sodium salt is achieved with reference to the foregoing structural formula when X, Y and Z are each hydrogen and accordingly has the formula:

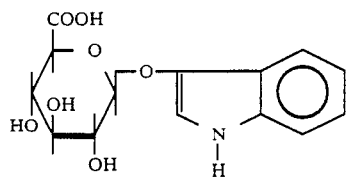

DETAILED EXPLANATION OF THE REACTION SCHEME

A process for the preparation of the reagents of the present invention has been developed by Drs. Saul Wolfe and Raymond Bowers of Queen's University in Kingston, Ontario, Canada. A typical reaction scheme according to such process using known starting materials for the production of the reagents of the present invention is as as shown in Chart I.

With reference to the said reaction scheme, methyl anthranilate (Formula II), prepared by known methodology from anthranilic acid, is reacted with the methyl ester of chloroacetic acid to give a compound of

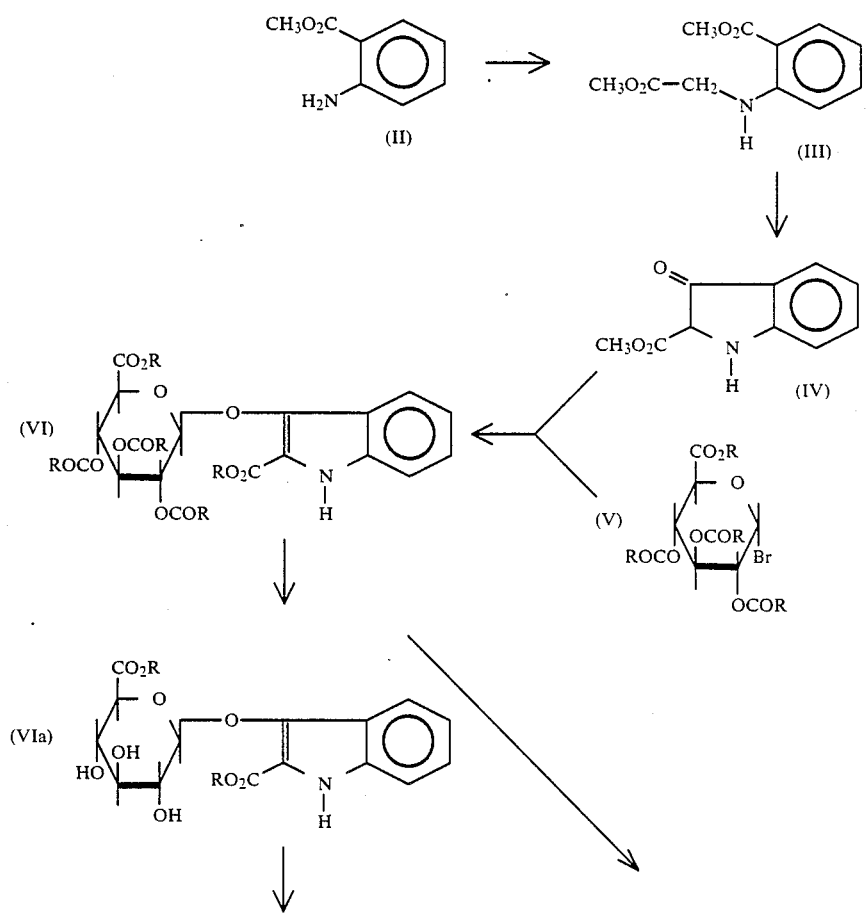

CHART I
REACTION SCHEME

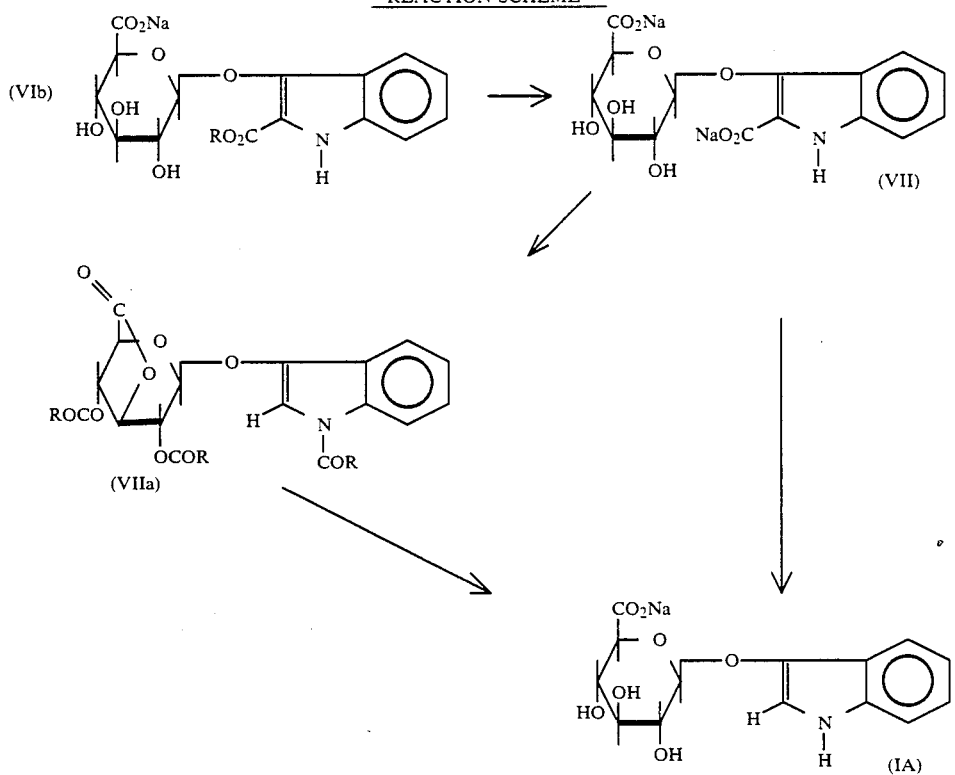

Formula III. The compound of Formula III is exposed to sodium metal to give the 2-carboxymethylindole of Formula IV.

Methyl [2,3,4-tri-O-acetyl-β-D-glucopyranosyl bromide]uronate of Formula V (where R is methyl), prepared by known techniques from glucuronic acid or glucuronolactone, is reacted with the 2-carboxymethylindole of Formula IV in water and methylene chloride containing an alkali metal hydroxide, preferably potassium hydroxide, and a phase transfer catalyst, such as tetra-n-butyl ammonium hydrogen sulfate to give methyl [(2-carboxymethylindol-3-yl)-2,3,4-tri-O-acetyl-β-D-glucopyranoside]uronate (Formula VI).

Reaction of the compound of Formula VI with five molar equivalents of NaOH in water and methanol gives disodium [(2-carboxyindol-3-yl)-β-D-glucopyranoside]uronate (Formula VII).

In the alternative, the compound of Formula VI may be reacted with barium methoxide to produce methyl [(2-carboxymethylindol-3-yl)-β-D-gluocopyranoside]uronate of Formula VIa, thereafter reacting the compound of Formula VIa with one equivalent of NaOH to produce sodium [(2-carboxymethylindol-3-yl)-β-D-gluocopyranoside]uronate of Formula VIb and thereafter reacting the compound of Formula VIb with a further equivalent of NaOH to produce the compound of Formula VII.

The compound of Formula VII may then be heated in water at 200°–250° C. in a pressure vessel to produce the sodium salt of indol-3-yl-β-D-glucuronic acid (or indoxyl-β-D-glucuronide)(Formula Ia) or alternatively may be deprotected with acetic anhydride and sodium acetate to produce [(N-acetylindol-3-yl)-2,4-di-O-acetal-β-D-glucopyranoside]uronate-3,6-lactone (Formula VIIa) which is then reacted with four equivalents of NaOH in water or methanol followed by evaporation and freeze-drying to give the compound of Formula Ia.

It will be appreciated by the skilled addressee that the above-detailed reaction scheme is intended to be representative only of one general reaction scheme which may be utilized in the preparation of the chromogenic reagents of the present invention. While the end product achieved by the reaction scheme may be the sodium salt of indoxyl-β-D-glucuronic acid, those skilled in the art would be able, without difficulty, to make appropriate substitutions to the reaction scheme including varying protecting groups, reaction conditions, starting materials and intermediates so as to prepare the members of the class of reagents envisaged by the present invention.

Also, members of the class of chromogenic reagents of the present invention have been disclosed and are commercially available and no claim is made herein to the said class per se.

For example, 5-bromo-4-chloroindoxyl-β-D-glucuronide (also known as 5-bromo-4-chloro-indol-3-yl-β-D-glucopyruroniside) was disclosed by Pearson et al. in 1967, who stated that the dicyclohexane amide salt of the compound was commercially available from Dr. Herman Plaut and staff at Cyclo Chemical Corporation, 1922 E. 64th Street, Los Angeles, Calif., U.S.A., 90001 (see Pearson et al "Histochemical β-Glucuronidase Distribution in Mammaliam Tissue as Detected by 5-bromo-4-chloroindol-3-yl-β-D-glucopyruroniside", *Laboratory Investigation* Vol. 17, No. 2, of 217, 1967). Most recently, 5-bromo-4-chloroindol-3-yl-β-D-glucuronide was disclosed by Jefferson, et al.("β-glucuronidase from *Escherichia coli* as a Gene-Fusion Marker" Proc. Natl Acad. Sci. U.S.A., Volume 83, pp.

8447-8451, November 1986) and is now commercially available from Research Organics Inc., 4353 East 49th Street, Cleveland, Ohio, U.S.A., 44125-1083 in the form of the cyclohexylammonium salt thereof (Catalogue No. 1177B).

It is to be pointed out that the various chemical names ascribed to the class of chromogenic reagents of the present invention are entirely interchangeable. Thus, indoxyl-β-D-glucuronide is interchangeable with indoxyl-β-D-glucuronic acid and indol-3-yl-β-D-glucuronic acid as is the somewhat outdated nomenclature β-D-glucopyruroniside which has generally been discarded in favour of β-D-glucuronide or β-D-glucuronic acid.

TEST EXAMPLE 1

This microtiter test was conducted to indicate the specificity of indoxyl β-D-glucuronide (IBGU) to *E. coli*.

250 ml of a BASAL agar growth medium were made up as follows on a g/l basis;

| INGREDIENT | AMOUNT |
| --- | --- |
| Proteose Peptone #3 | 5.0 g. |
| Yeast Extract | 3.0 g. |
| Glycerol | 10.0 g. |
| NaCl | 7.5 g. |
| $K_2HPO_4$ | 3.3 g. |
| $KH_2PO_4$ | 1.0 g. |
| Sodium lauryl sulphate | 0.2 g. |
| Sodium desoxycholate | 0.1 g. |
| Agar | 15.0 g. |
| Distilled $H_2O$ | to volume of 1000 ml. |

The BASAL agar growth medium was then steam autoclaved for 15 minutes at 121° C. and 15 psi.

Four batches of 25 ml. each were then taken from the total 250 ml. To the first batch was added 0.0150 g. of the sodium salt of indoxyl-β-D-glucuronide (IBGU). To the second batch was added 0.0097 g. p-nitrophenyl-β-D-glucuronide (PNG). To the third batch was added 0.0079 g. indoxyl β-D-glucoside (INDICAN). The fourth batch was left untreated (BASAL).

Five samples of 2 ml each were taken out of each of the 25 ml batches referred to above giving a total of twenty samples. Four of the samples from each batch were then inoculated with four bacterial strains as shown below. The negative (control) samples were not inoculated. The incubation time for the test was 16±1 hour at 45° C.

The results of the microtiter specificity test are shown in Table 1 below.

TABLE 1

| | MICROTITER SPECIFICITY TEST | | | | |
| --- | --- | --- | --- | --- | --- |
| | BACTERIUM | | | | |
| MEDIUM | E. coli ATCC 35218 | K. pneumonia ATCC 13883 | E. coli 83-17350 | K. pneumonia PHL (Public Health Lab) | Negative (Control) |
| BASAL | − | − | − | − | − |
| IBGU | + | − | + | − | − |
| PNG | + | − | + | − | − |
| INDICAN | − | + | − | + | − |

The PNG and the INDICAN provided positive and negative controls respectively for determining the presence of *E. coli*. Note that wherever a negative sign appears on the chart above, this indicates no colour change, a plus sign indicates a blue colour in the case of INDICAN and IBGU and a yellow colour in the case of PNG. ATCC bacterial strains were from the American Type Culture Collection, Rockville, Md., U.S.A.; *E. coli* 83-17350 is an isolate from the Ontario Ministry of Environment, Kingston Regional Laboratory, Kingston, Ontario, Canada; and *Klebsiella pneumonia* PHL was obtained from the Ontario Ministry of Health, Kingston Regional Laboratory, Kingston, Ontario.

Table 1 above shows that IBGU reacts in a manner similar to that observed for the positive control PNG and that the IBGU has no activity with either of the Klebsiella strains which do not have the capacity to synthesize the enzyme β-glucuronidase. These results indicate that IBGU, when incorporated into an agar growth medium, can be used for the qualitative detection of *E. coli* in a test specimen.

TEST EXAMPLE 2

This test was conducted to illustrate the specificity of indoxyl-β-D-glucuronide to *E. coli*, when the bacterium has been cultured on the surface of a suitable membrane filter. In order to do so, the tests were performed using gridded membrane filters that are recommended for use in the bacteriological analysis of drinking water as described in the Ontario Ministry of the Environment, Handbook of Analytical Methods of Environmental Samples, December, 1983.

Two samples each of 2 ml were taken from each of the four batches of IBGU (sodium salt), PNG, INDICAN and BASAL agar growth media as prepared in Example 1 and applied to eight petri dishes giving, in total, eight samples. A single membrane filter (Gelman, gridded GN-6, 0.45 micron) was then applied to the surface of the agar medium in each petri dish before inoculation with bacteria.

A first group of four membrane filters was then inoculated by transferring *E. coli* ATCC 35218 with a toothpick to the upper half of each filter and to the lower half of each of these same filters transferring *K. pneumonia* ATCC 13883 both being the same strains as used in Example 1. A second group of four membrane filters was then prepared by inoculating, in the manner described immediately above, the upper half of each filter with *E. coli* 83-17350 and the lower half of these same four filters with the PHL *K. pneumonia* again as used in Example 1. The total of eight membrane filters were thus inoculated with bacteria for incubation on the treated growth media in the eight petri dishes. Each of the dishes was then incubated for about 14 hours at 45° C.

Following incubation a series of discrete and readily distinguishable indigo blue colonies appeared on the upper half (i.e. the half inoculated with *E. coli*) of the membrane filters placed on the IBGU growth medium. A series of clear colonies appeared on the lower half of each of these same two filters. In contrast the two filters placed on the INDICAN medium showed a reverse situation in which a series of blue dots (colonies) appeared on the lower half (i.e. the half inoculated with *K. pneumonia*) while a series of clear colonies appeared on the upper half of each of these filters. *E. coli* and Klebsiella strains, inoculated on the upper and lower half of the membrane filter grew as colourless colonies after incubation on the BASAL medium. On the PNG medium, *E. coli* colonies produced a small amount of yellow colour below the surface of the membrane filter as a result of the hydrolysis of PNG, but the colour of the individual *E. coli* colonies was not clearly distinguishable from the yellow background.

These test results not only show the positive indication of *E. coli* in the presence of IBGU, but also demonstrate that the colonies grown from *E. coli* cells, deposited on a membrane filter and incubated in the presence of IBGU, can be readily distinguished from bacterial colonies of *Klebsiella pneumonia* that have grown under the same conditions of incubation and on the same membrane filter.

TEST EXAMPLE 3

Twelve pure isolates or colony cultures obtained from the Ontario Ministry of Environment Laboratory Services Branch in Rexdale, Ontario, Canada were transferred with a wooden applicator stick to membrane filters preapplied to a BASAL agar growth medium as prepared in Example 1 containing the sodium salt of IBGU. The cultures were then incubated at a temperature of 35° C. for about 18 hours after which the colour of each of the isolates or cultures was assessed as shown in Table 2 below.

TABLE 2

| ISOLATES | COLOUR |
|---|---|
| 1. *Escherichia coli* (stock #3) | blue colony |
| 2. *Klebsiella pneumoniae* (stock #7) | cream colony |
| 3. *Salmonella typhimurium* (stock #4) | cream colony |
| 4. *Streptococcus faecalis* (stock #10) | no growth |
| 5. *Staphylococcus aureus* (stock #5) | cream colony |
| 6. *Pseudomonas aeruginosa* (stock #21) | cream colony |
| 7. *Bacillus sp.* (stock #22) | no growth |
| 8. *Acinetobacter calcoaceticus* (stock #64) | cream colony |
| 9. *Bacillus sp.* (stock #125) | no growth |
| 10. *Aeromonas hydrophila* (stock #39) | cream colony |
| 11. *Enterobacter cloacae* (0640-C) | cream colony |
| 12. *Escherichia coli* (weak fluorescent positive on MUG) | blue halo surrounding cream colony |

The test results show that *E. coli* was the only organism producing a blue colony in the presence of IBGU. These results thus demonstrate both the high degree of specificity and selectivity of IBGU to *E. coli*, when this organism is cultured on a membrane filter on an agar growth medium at 35° C. in the presence of IBGU.

TEST EXAMPLE 4

Three different *E. coli* isolates comprising a strong, a weak and a non-glucuronidase strain as well as an isolate of *Klebsiella pneumonia* were tested. All isolates were seeded to membrane filters by filtering appropriate dilutions of the bacterial isolates through the membrane filter and then transferring the filter onto BASAL agar growth medium treated with the sodium salt of IBGU and then incubating the filters on the medium at 44.5° C. for 18 to 20 hours. The strong and the weak glucuronidase strains of *E. coli* produced blue colonies while the non-glucuronidase strain (reference number 0157:H7, Ontario Ministry of Health), of *E. coli* did not show any growth.

The *Klebsiella pneumonia* produced a slightly yellow colony on the medium described above, and the *Klebsiella pneumonia* colony was easily visually distinguishable from the blue *E. coli* colonies.

TEST EXAMPLE 5

Ten environmental *E. coli* isolates from eight different bathing beach samples were tested. The pure cultures were spot innoculated onto a membrane filter previously placed on BASAL agar growth medium with the sodium salt of IBGU added and then incubated for 18 to 20 hours at 44.5° C. The *E. coli* isolates from all samples were readily identified in the form of discrete blue colonies which could easily be counted on the gridded membrane filters.

TEST EXAMPLE 6

The following membrane filtration test was performed to determine the validity of testing for *E. coli* using IBGU by identifying the genus and species of bacteria which were recovered fron environmental samples and which grew as blue or colourless colonies on an agar growth medium containing IBGU.

Various different "blind" samples, as shown in Tables 3 and 4 below, were assayed using membrane filters placed on BASAL agar growth medium treated with the sodium salt of IBGU. Following incubation, both blue and clear colonies appeared on the individual membrane filters which were used for the analysis of the various different samples. Table 3 shows, in Column A, that 61 blue colonies appeared. These individual colonies were then retested using API 20E (Analytical Profile Index, Analytab Products, Division of Ayerst Laboratories, 200 Express Street, Plainview, N.Y., 11803, U.S.A.) test strip method to determine how many of these colonies were actually *E. coli* or at least contained *E. coli*, the results of which retesting are shown in Column B of Table 3.

TABLE 3

| SAMPLE | SOURCE | COLUMN A BLUE COLONIES Tested | COLUMN B % E. Coli (or containing E. coli) |
|---|---|---|---|
| 1694 | Storm Sewer (Young's Creek) | 44 | 100% |
| HR | Humber River | 6 | 100% |
| 1890 | Centennial Park Sewer (St. Catherines Study) | 2 | 100% |
| 2793 | Pulp and Paper final effluent (St. Catherines) | 9 | (8/9) = 88.9% |

TABLE 3-continued

| SAMPLE SOURCE | COLUMN A BLUE COLONIES Tested | COLUMN B % E. Coli (or containing E. coli) |
|---|---|---|
| TOTAL BLUE COLONIES | 61 | (60/61) = 98.4% |

Table 4 shows, in Column A, the number of background or cream colonies found in the various test samples. These cream colonies were then retested using the standard API test strip method to determine if any of these colonies contained E. coli, the results of which retesting are shown in Column B of Table 4.

TABLE 4

| SAMPLE | SOURCE | COLUMN A BACKGROUND (cream) (Colonies tested) | COLUMN B % E. coli |
|---|---|---|---|
| 1694 | Storm Sewer (Young's Creek) | 8 | 1/8 = 12.5% |
| HR | Humber River | 8 | 2/8 = 25% |
| 1890 | Centennial Park Sewer (St. Catherines) | 8 | 0 |
| 2793 | Pulp and Paper Effluent (St. Catherines) | 4 | 0 |
| | TOTAL | 28 | (3/28) = 10.7% |

As will be seen above in Table 3, out of the total of 61 blue colonies tested, 60 of those were confirmed as E. coli, giving an accuracy rate of 98.4%. In Table 4, it will be seen that, out of the 28 colonies appearing as cream colonies, three of these actually contained E. coli. These three E. coli containing colonies were then retested using the sodium salt of IBGU and the cream colony from the 1694 sample then produced a blue colony. The other two HR cream samples continued to produce a cream colour when retested on the IBGU treated medium.

The results of the overall test show that, out of the total of 63 E. coli colonies actually present, 60 of these gave the desired target reaction for an accuracy rate of 95.2%.

What is claimed is:

1. A method of determining the presence of E. coli, having glucuronidase activity, contained in a liquid sample, said method comprising:

(a) passing a predetermined amount of said sample through a membrane filter arranged to retain said E. coli thereon while passing said liquid sample therethrough;

(b) contacting said filter with a chromogenic reagent comprising indoxyl-$\beta$-D-Glucuronide or a salt thereof contained in an E. coli nutrient medium; and (c) incubating said filter whereby the chromogenic reagent is subjected to said glucuronidase activity so as to produce clearly defined indigo blue coloring representative of individual colonies of any E. coli cells present on said membrane filter.

2. A method as claimed in claim 1 including the step of counting said colonies and thereby enumerating said E. coli.

3. A method, as claimed in claim 1, wherein said membrane filter is incubated for a period of about 14 to 24 hours at a temperature from about 35° C. to 45° C.

4. A method, as claimed in claim 3, wherein said membrane filter is provided with a grid pattern for facilitating counting of the individual E. coli colonies.

5. A method, as claimed in claim 1, wherein about 0.3 to 0.8 grams chromogenic reagent is added per liter of nutrient medium.

* * * * *